United States Patent [19]

Wong

[11] Patent Number: 5,110,290
[45] Date of Patent: May 5, 1992

[54] ORTHODONTIC BRACKET/MESH SCREEN

[75] Inventor: Raymond F. Wong, Chino, Calif.

[73] Assignee: Ormco Corporation, Glendora, Calif.

[21] Appl. No.: 615,491

[22] Filed: Nov. 19, 1990

[51] Int. Cl.$^5$ .................................................. A61C 3/00
[52] U.S. Cl. ............................................ 433/9; 433/24
[58] Field of Search ........................................ 433/8, 9, 24

[56] References Cited

U.S. PATENT DOCUMENTS

| | | | |
|---|---|---|---|
| 4,068,379 | 1/1978 | Miller et al. | 433/9 |
| 4,165,561 | 8/1979 | Miller et al. | 433/9 |
| 4,172,323 | 10/1979 | Orlowski | 433/9 |
| 4,256,455 | 3/1981 | Förster | 433/8 |
| 4,360,342 | 11/1982 | Salvo | 433/172 |
| 4,433,960 | 2/1984 | Garito | 433/215 |
| 4,479,527 | 10/1984 | Boettcher | 164/34 |
| 4,889,485 | 12/1989 | Iida | 433/9 |
| 4,927,361 | 5/1990 | Smith et al. | 433/9 |
| 4,948,366 | 8/1990 | Horn et al. | 433/9 |

OTHER PUBLICATIONS

Comparisons of different debonding techniques for ceramic brackets: An in vitro study Samir E. Bishara, DDS, BDS, D. Ortho., MS* Timothy S. Trulove, DDS, MS**-Aug., 1990 pp. 145-153.

*Primary Examiner*—Cary E. O'Connor
*Assistant Examiner*—Cindy A. Cherichetti
*Attorney, Agent, or Firm*—Wood, Herron & Evans

[57] ABSTRACT

An orthodontic appliance for attachment to a tooth having a ceramic engaging surface for attachment to the tooth. A single compliant layer having a plurality of openings is accrued to the engaging surface of the tooth. The appliance is attached to the surface of the tooth using a chemically active adhesive system.

13 Claims, 2 Drawing Sheets

ORTHODONTIC BRACKET/MESH SCREEN

BACKGROUND OF THE INVENTION

This invention relates to orthodontic appliances. More particularly, the present invention is directed to an orthodontic appliance and method of making same which has been designed to be reliable, low cost, easy to manufacture, provides controlled debonding characteristics, and does not interfere with the aesthetic appearance of the appliance.

Aesthetically pleasing orthodontic appliances have become quite popular in the marketplace Typically, these orthodontic appliances are made of a substantially clear or translucent ceramic material. Examples of ceramic materials being used are crystalline alumina, glass and zirconium. In order to properly secure these type orthodontic brackets to the teeth, a chemically reactive-type adhesive system is used. While these chemically reactive bonding systems provide very high bond strengths, which is desirable for maintaining brackets securely on the tooth, the high bond strength can present a problem when the orthodontic bracket is to be removed. The high bond strengths, often obtained by these adhesive systems, present the possibility that tooth enamel will be removed during the bracket removal process.

Applicants have invented an improved orthodontic appliance and a method of making the appliance, which controls the debonding force necessary to remove the appliance and thus minimize the possibility of enamel removal, is easy to assembly, low cost to manufacture and still provides an aesthetically pleasing appliance.

SUMMARY OF THE INVENTION

In one aspect of the present invention, there is provided an orthodontic appliance designed for attachment to a tooth. The appliance includes a base portion made of ceramic material having an engagement surface for placement against the tooth. A single layer of a compliant material is disposed adjacent the engagement surface. The compliant layer has a plurality of openings for allowing adhesive to pass therethrough and is made of a material which substantially chemically inert so as to not form any substantial part of adhesive chemical bond.

In another aspect of the present invention, there is provided a method of controlling the bonding/debonding characteristic between a dental appliance having a ceramic engaging surface and a tooth. The method comprises the steps of:

(a) applying an organofunctional promoter onto the engaging surface;

(b) applying a barrier layer of a compliant material having a plurality of openings for allowing adhesive to flow therethrough, the barrier layer being made of a material which is substantially non-reactive with respect to said chemical bonding system;

(c) applying a chemically active adhesive to the engaging surface;

(d) placing said bracket onto the tooth; and (e) curing the adhesive.

DETAILED DESCRIPTION OF THE INVENTION

Figure 1:
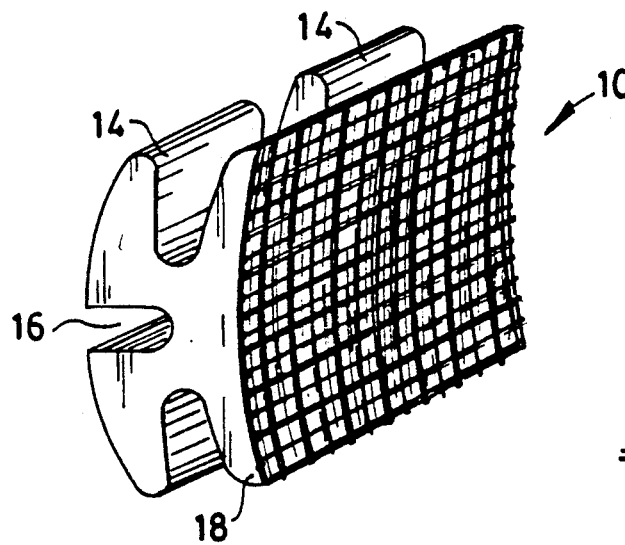
FIG. 1 is a perspective view of an orthodontic appliance assembly made in accordance with the present invention.
Figure 2:
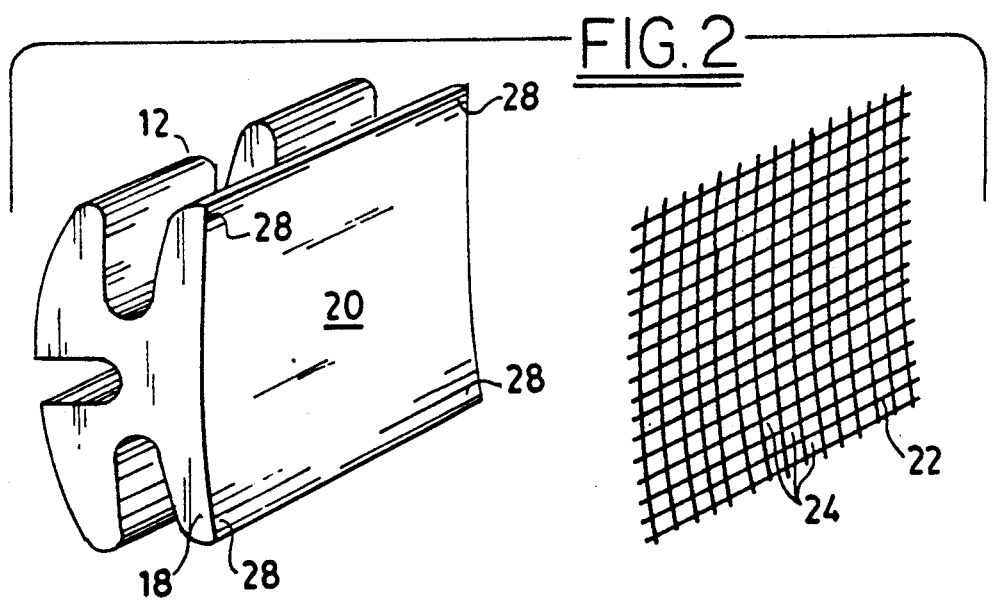
FIG. 2 is an exploded view of the orthodontic appliance assembly of FIG. 1.
Figure 3:
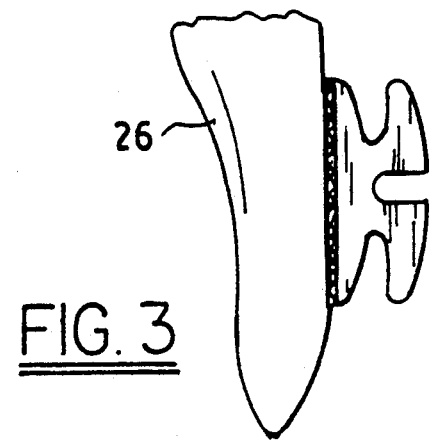
FIG. 3 is a side elevational view of the orthodontic bracket assembly of FIG. 1 as bonded to the tooth of a patient.
Figure 4:
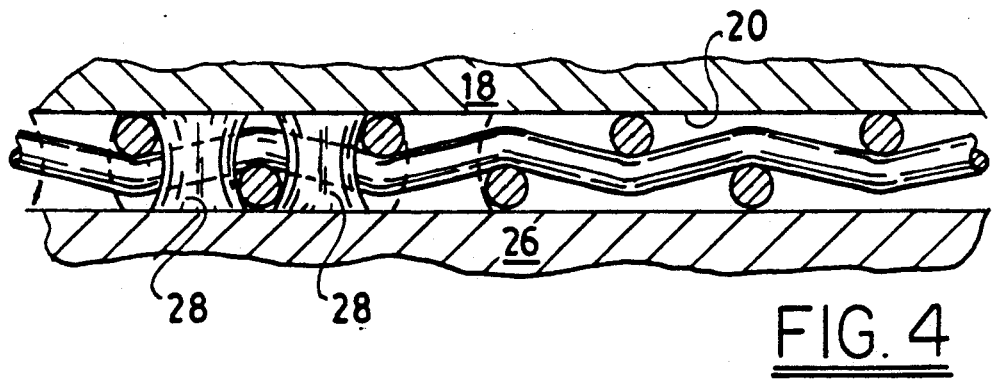
FIG. 4 is an enlarged fragmentary cross-sectional view of the area between the orthodontic appliance and the tooth illustrating the adhesive flow pattern therebetween.
Figure 5:
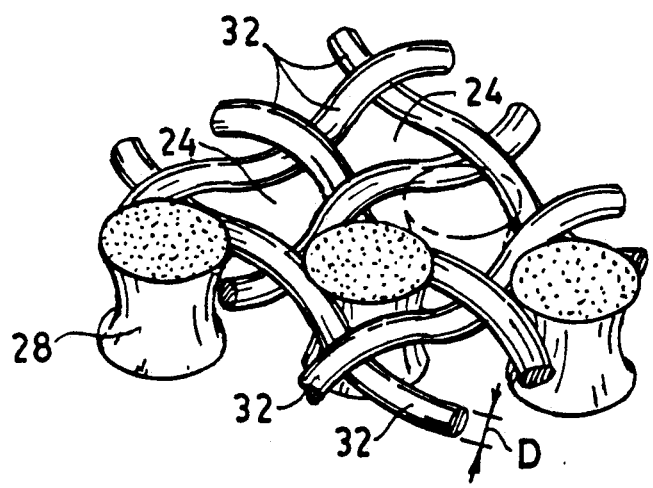
FIG. 5 is a enlarged perspective view of the adhesive bond section of FIG. 4 between the tooth and bonding surface of the bracket.

Referring to the Figures, there is illustrated an orthodontic appliance assembly 10 made in accordance with the present invention. In the particular embodiment illustrated, the orthodontic appliance assembly 10 is an orthodontic bracket assembly. However, it is to be understood that the orthodontic appliance 10 may be any other appliance that is secured to a tooth. The orthodontic bracket assembly 10 comprises a main body portion 12 which is typical of prior art orthodontic bracket. The body section 12 includes a pair of viewings 14 which form an archwire slot 16 for receiving a typical orthodontic archwire and a base portion 18 having bonding surface 20 designed to be secured to a tooth. As is typical in orthodontic brackets, bonding surface 20 is a doubly curved concave surface and primarily contacts the tooth at the four corners. In the particular embodiment illustrated body section 12 is of a twin tiewing construction, however, the present invention is not limited to such and the body section 12 may be of any desired configuration. The main body section 12 is made of a ceramic material. In the particular embodiment illustrated, the main body section 12 is made of polycrystalline alumina which is substantially transparent. The main body section 12 may be formed in any conventional manner as is well known in the prior art. An example of such a bracket available in the prior art is produced and sold by Ormco Corporation under the LUMINA trademark.

A mesh screen 22 made of a compliant material is secured to bonding surface 20. Mesh screen 22 acts as barrier layer and is designed to provide a plurality of independent passages 24 for allowing the orthodontic adhesive used to pass therethrough and thus secure the bracket to the tooth. The mesh screen 22 is preferably made of a color stable material. It is desired that mesh screen 22 does not form a part of the bonding structure, thus mesh screen 22 should be chemically non-reactive with respect to the adhesive used to bond the bracket to the tooth. The screen should be flexible so as to not form a part of the adhesive bond strength. It is important that it is sufficiently flexible so as not to transmit any substantial force therethrough. In order not to interfere with aesthetic appearance of the body section 12, the mesh screen is preferably clear or translucent and is resistant to staining or yellowing over time. Applicant found that a low density polyethylene is substantially translucent and is highly resistant to staining. The mesh screen 22 is preferably made of a monofilament cords 32 that are woven in a typical weave pattern. In the particular embodiment illustrated, the cords 32 have a diameter D of about 0.003 inches 0.0762 mm). Applicants have found that a woven polyethylene monofilament cloth, sold by Tetko Inc., Cat. No. 8-156-100, works quite satisfactorily. The passages 24 in mesh screen 22 allows the orthodontic adhesive used to secure bracket 10 to tooth 26 to flow therein so as to form a plurality of independent neck segment 28 which secure the bonding base 16 to the tooth surface 22. The mesh screen 22 also serves to provide a fracture plane which assists in the debonding of the orthodontic assembly 10 from the tooth 26. By controlling the size and number of passages 18 the debonding loads necessary to remove the bracket is within a desired range. Applicants found that shear debonding loads in the range of 10-20 kg at a strain rate of 0.5 mm/min., tensile debonding loads in the range of about 6-12 kg and impact loads of less than about 3 kg are desired. Preferably shear debonding loads range from about 10 to 12 kg, tensile loads range from about 8 to 10 kg and impact loads range are less than about 2 kg.

The bonding surface 20 is first treated so as to set up the proper chemistry for bonding to the tooth. For this purpose an organofunctional promoter is first applied to the engaging surface 20, typically a silane promoter is employed. After the silane treatment is complete, the mesh screen 22 is applied.

The mesh screen 22 may be applied to the bonding base 20 in any appropriate manner. Applicants found that the mesh screen 22 may be applied by at least two different methods. In the first method, the bonding base 12 is painted with a thin film of a light cure adhesive sealant. Applicants have found that a sealant sold by Unitek under the trademark TRANSBOND can be used. The film is then partially cured with an appropriate light so that the sealant becomes tacky. Applicants have found that exposing the sealant to a U.V. light for about three seconds will provide the desired tackiness. A mesh screen 22 having an overall size and configuration which substantially conforms to the outer configuration of the bonding surface 20 is positioned against the bonding surface 20 and a light pressure is applied to secure it to the bonding surface 20. The sealant is then finally cured with a second application of light. This results in the mesh screen 22 being semi-encapsulated. Any excess sealant or mesh screen hanging over the sides of the bonding surface 20 may be trimmed by any hot knife technique convenient to the user.

A second method of applying mesh screen 22 to bonding surface 20 comprises the use of a light cure sealant of the type previously described. However, instead of coating the entire surface of base surface 20, only each of the corners 29 have sealant applied thereto. The screen is carefully positioned so as to encapsulate only the corners of the screen with the sealant. The sealant is then cured with an appropriate light source. The TRANSBOND sealant was also found suitable for this method.

After the mesh screen 14 has been secured to bonding base 20, the bracket is secured to the tooth in typical prior methods employed. A chemically active adhesive is applied to bonding base 16, for example, System 1+sold by Ormco Corporation. Thereafter, the orthodontic bracket assembly 10 is placed against the tooth 24 and the adhesive is allowed to cure as is cured as typically done in the in the prior art. For example, through the use of a self-cure adhesive system or the use of a lightcure system.

Figure 6:
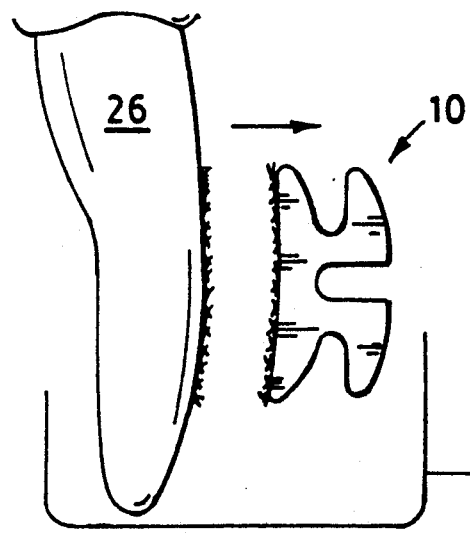
FIG. 6 is a side elevation of a tooth from which the orthodontic appliance of FIG. 1 has been removed.

In a test of the present invention, a mesh screen made of a polyethylene material from Tetko Inc. (Cat. No. 8-156-100) having a mesh size of $100 \times 156$ openings per inch was bonded to an orthodontic bracket made of polycrystalline alumina. The bracket had a bonding surface 20 with a surface area of about 0.014 $in^2$. The bonding surface 20 was first subjected to silane treatment. A mesh screen 22 was then secured to surface 20 by one of the above teachings using TRANSBOND sealant. The bracket assembly 10 was then secured to the tooth using Concise (3M) adhesive described above. In debonding tests orthodontic brackets made in or mesh/adhesive interface leaving the tooth enamel fully in tack on the tooth as illustrated in FIG. 6. Thus the present invention was able to provide uniform bond strengths within the desired strengths which minimized the potential damage to the tooth enamel during debonding of the bracket After removal of the appliance, standard deburring techniques can be used to remove any adhesive or mesh screen remaining on the tooth 26. Since mesh screen is made of a soft compliant material, this removal process is accomplished quickly without any substantial discomfort to the patient.

It is to be understood that various modifications and changes may be made without departing from the scope of the present invention. For example, but not by way of limitation, various other flexible material may be used. Additionally, while barrier layer is preferably a mesh screen, the barrier layer may take other forms such as a sheet of polyethylene having a plurality of openings, so long as the barrier layer does not form a chemical bond with the adhesive system.

What is claimed is:

1. An orthodontic appliance for attachment to a tooth, said appliance comprising:
   (a) a base portion made of a ceramic material, said base portion having an engagement surface for placement against said tooth; and
   (b) a single barrier layer of a compliant material placed adjacent said engagement surface, said single layer having a plurality of independent passages for allowing an adhesive to pass therethrough for securing said base portion to said tooth, said barrier does not form a part of the bond structure between the appliance and tooth and is made of a material which is sufficiently flexible so as to not transmit any substantial forces therethrough and is substantially chemically inert so as to not form any substantial adhesive chemical bond with said adhesive, said layer providing a fracture plane for assisting in debonding said appliance from said tooth.

2. An orthodontic appliance according to claim 1 wherein said single barrier layer is made out of a fabric mesh of a polyethylene material.

3. An orthodontic appliance according to claim 2, said fabric mesh having $100 \times 156$ openings per inch.

4. An orthodontic appliance according to claim 1 wherein said base portion is made of a ceramic material selected from one of the following: single crystal alumina, polycrystal alumina, zirconia, glass.

5. The orthodontic appliance according to claim 1 wherein said adhesive forms a plurality of neck segments which extend through said openings in said layer, said neck segments providing a bond strength no greater than about 0 kg at strain rate less than 5 mm/min.

6. An orthodontic appliance according to claim 1 wherein said base portion has a substantially rectangular configuration, said engaging surface being concave such that when the bracket is secured to said tooth, the primary contact occurs at the four corners of said engaging surface.

7. An orthodontic appliance according to claim 1 wherein an organofunctional promoter is applied to said engaging surface of said base portion.

8. An orthodontic appliance according to claim 7 wherein said adhesive is designed to chemically bond to said organofunctional promoter.

9. A method for controlling the debonding characteristics between dental appliance having a ceramic engaging surface and a tooth whereby a chemically bonding system is employed for secured said appliance to said tooth, comprising the steps of:
  (a) applying an organofunctional promoter onto said engaging surface;
  (b) applying a barrier layer of a compliant material having a plurality of openings for allowing adhesive to flow therethrough, said barrier layer being made of a material which is sufficiently flexible so as to not transmit any substantial forces therethrough and is substantially non-reactive with respect to said chemical bonding system;
  (c) applying a chemically active adhesive to said engaging surface;
  (d) placing said bracket onto said tooth; and
  (e) curing said adhesive.

10. A method according to claim 9 wherein said organofunctional promoter is silane.

11. A method according to claim 9 wherein said barrier layer is made of a polyethylene mesh having 100×156 openings per inch.

12. A method according to claim 11 wherein said mesh is made of a fabric composed of filaments having a diameter of about 0.003 inches.

13. A dental assembly comprising:
  (a) a dental appliance having a ceramic bonding engagement surface which is secured to said tooth of a patient;
  (b) a compliant barrier layer made of a non-active chemically inert material which does not form part of the bond structure between the appliance and tooth, and is sufficiently flexible so as not to transmit any substantial forces therethrough said barrier layer having a plurality of openings therethrough; and
  (c) a chemically active adhesive layer between said dental appliance and said tooth.

* * * * *

UNITED STATES PATENT AND TRADEMARK OFFICE
CERTIFICATE OF CORRECTION

PATENT NO. : 5,110,290
DATED : May 5, 1992
INVENTOR(S) : Raymond F. Wong

It is certified that error appears in the above-identified patent and that said Letters Patent is hereby corrected as shown below:

```
At column 2, line 27, "viewings" should be --tiewings--.
At column 2, line 68, please insert --(-- after "inches" and
 before 0.0762mm).".
At column 4, lines 10-11, after "made in" and before "or"
 please insert --accordance with the present invention were
 found to debond at the mesh/bracket--.
At column 4, line 63, "0" should be --20--.
```

Signed and Sealed this

Seventh Day of September, 1993

Attest:

BRUCE LEHMAN

Attesting Officer     Commissioner of Patents and Trademarks